United States Patent
Baudino et al.

(10) Patent No.: US 6,210,417 B1
(45) Date of Patent: Apr. 3, 2001

(54) MEDICAL LEAD POSITIONING AND ANCHORING SYSTEM

(75) Inventors: Michael D. Baudino, Coon Rapids; Thomas E. Cross, Jr., St. Francis, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/302,085

(22) Filed: Apr. 29, 1999

(51) Int. Cl.$^7$ ...................................................... A61M 5/32
(52) U.S. Cl. ........................... 606/129; 604/175; 607/116
(58) Field of Search ................................ 607/1, 2, 45–46, 607/116, 139; 600/377, 378, 383, 386; 604/175; 606/108, 129, 130

(56) References Cited

U.S. PATENT DOCUMENTS

| | | |
|---|---|---|
| 4,328,813 | 5/1982 | Ray ........................................ 128/791 |
| 4,350,159 | 9/1982 | Gouda .................................... 128/303 |
| 4,805,634 * | 2/1989 | Ulrich et al. .......................... 600/561 |
| 5,464,446 | 11/1995 | Dreessen et al. ...................... 607/116 |
| 5,662,600 | 9/1997 | Watson et al. ............................ 604/8 |
| 5,865,842 * | 2/1999 | Knuth et al. ........................... 607/116 |
| 5,927,277 * | 7/1999 | Baudino et al. ....................... 607/116 |
| 6,044,304 * | 3/2000 | Baudino ................................ 607/116 |

* cited by examiner

*Primary Examiner*—Jeffrey R. Jastrzab
(74) *Attorney, Agent, or Firm*—Banner & Witcoff, Ltd.

(57) ABSTRACT

There is disclosed a medical apparatus for positioning and anchoring a lead to a cranium burr hole. The apparatus comprises generally a sleeve and a plurality of springs positioned within the sleeve. The apparatus may be inserted within a conventional burr hole ring or serve as a stand-alone anchoring device that fits within a burr hole. Once a lead is inserted into the sleeve between the plurality of springs, the springs exert a radial force on the lead body, thereby holding the lead in the desired position. The apparatus may also include a circular disc, defining a slot, mountable within the burr hole ring. The circular disc permits the selective positioning of the lead within the burr hole.

48 Claims, 1 Drawing Sheet

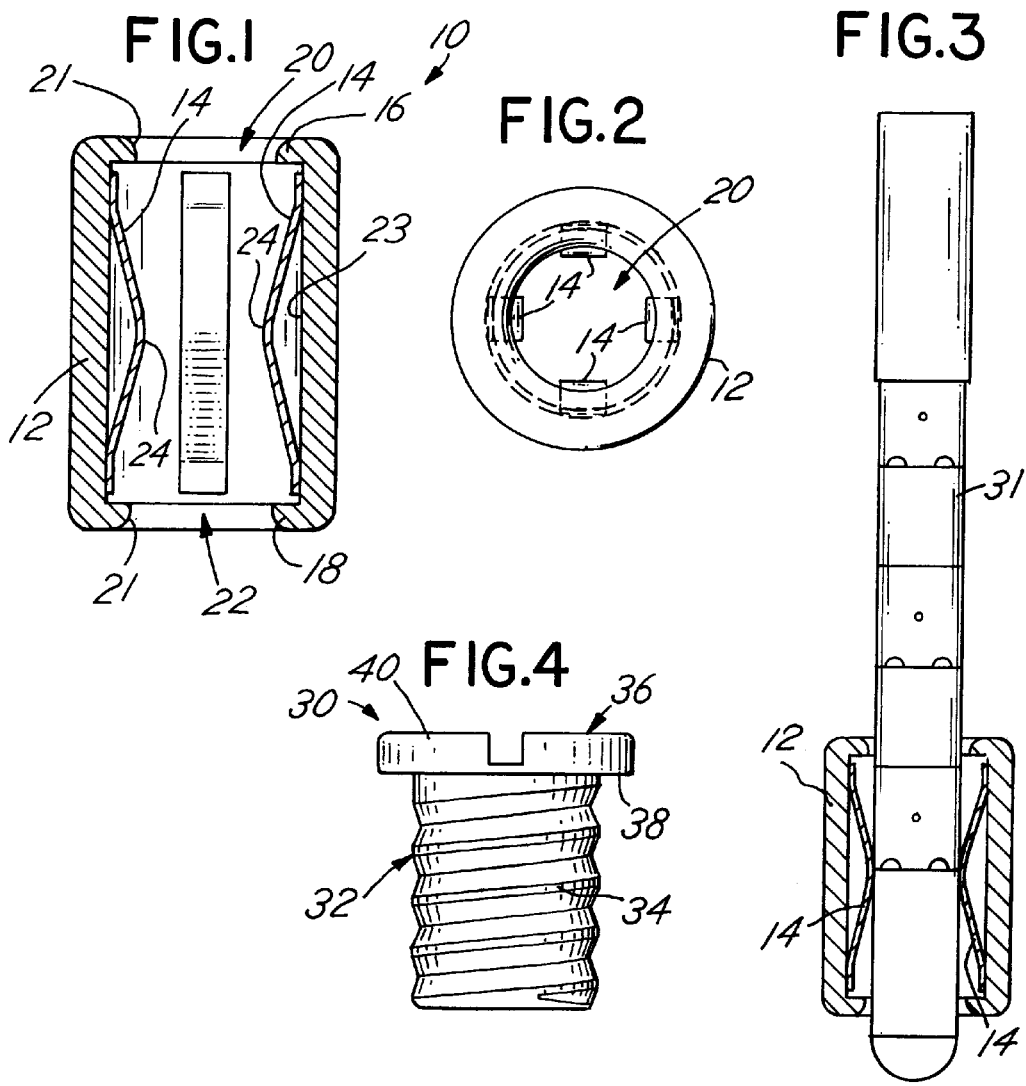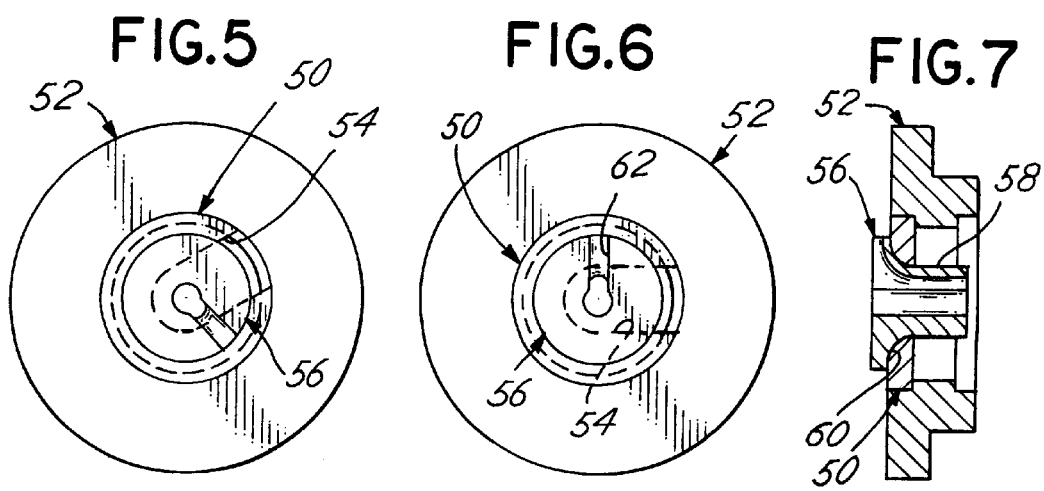

MEDICAL LEAD POSITIONING AND ANCHORING SYSTEM

BACKGROUND OF THE INVENTION

1. Field of the Invention

The present invention relates to an apparatus for securing implanted medical devices and more particularly to an apparatus for securing implanted medical devices such as electrical stimulation leads or catheters, or a combination thereof, within a cranial burr hole and for varying the functional location of the leads or catheters within the burr hole.

2. Description of the Related Art

Medical procedures involving access to the brain through a burr hole in the skull are under increasing use. Two such procedures are electrical stimulation of the brain for such purposes as relief of chronic pain and treatment of movement disorders, and the use of parenchymal catheters for infusing pharmaceutical agents. A typical electrical brain stimulation system comprises generally a pulse generator operatively connected to the brain by a lead having at its distal end at least one electrode designed to be implanted within the brain, and having at its proximal end a connector assembly designed to connect to the pulse generator. Use of a parenchymal catheter generally involves the insertion of a catheter within the brain to dispense pharmaceutical agents at a specific targeted location.

An important aspect of these procedures, and of any other such procedures that involve instrument access to the brain through a burr hole, is the precision with which any such inserted stimulation devices are placed. As can be appreciated, the functional location of the inserted stimulation device is of critical importance and once an inserted device is properly positioned, it is equally important that the device not be moved. Even one millimeter of travel of a properly positioned stimulation device may cause unsatisfactory results or, in some cases, severe injury to the brain. Accordingly, reliable methods and apparatus for locating and fixing the positioned stimulation device in the cranium burr hole are necessary.

Previous designs of systems for securing a positioned device within a burr hole have a number of drawbacks. U.S. Pat. No. 4,328,813 issued to Ray, incorporated herein by reference, discloses a burr hole ring and cap arrangement in which the cap is positioned so as to trap a positioned electrical stimulation lead between the ring and cap by friction. That arrangement involves securing the lead off center from the burr hole in a manner such that during installation of the anchoring cap the lead is secured in place. The lead, however, often needs to be manually supported in place while the anchoring cap is being installed. The lead is thus susceptible to inadvertent movement by the physician during the cap installation period. Further, during the interaction of the cap and ring, the lip of the cap tends to pull on the lead dislodging the lead from the targeted stimulation area.

Other current burr hole rings and caps force the lead body to the center of the burr hole ring and, due to the design, to the center of the burr hole itself. Problems occur if the burr hole is not centered on the desired projection path of the lead. The burr hole ring will force the lead body to the center of the burr hole ring, which is offset from the desired lead projection path, thereby placing a load on the lead body tip, which is implanted at the targeted stimulation area in the brain. The load on the lead body tip may force the electrodes away from the targeted stimulation area or it may place an undesirable amount of pressure on the brain. The present invention is directed to overcoming the disadvantages of the foregoing systems.

SUMMARY OF THE INVENTION

As explained in more detail below, the present invention overcomes the above-noted and other shortcomings of prior burr hole anchoring devices.

The present invention preferably comprises an apparatus fixing a lead at a cranial burr hole. One significant feature of the invention anchors the lead before the placement of a cap over the burr hole, thereby reducing the possibility of lead movement. This feature can be implanted directly into a cranium burr hole or it can be installed into a standard burr hole ring which is then implanted into the burr hole. A second significant feature of the present invention functionally locates the lead within a standard burr hole ring, thereby improving the location of the lead at the targeted stimulation area and reducing the possibility of injury to the brain.

Briefly, the present invention comprises several embodiments, more fully discussed below. One embodiment generally incorporates a cylindrical sleeve and a plurality of springs mounted within the cylindrical sleeve. The lead is inserted through the cylindrical sleeve between the plurality of springs which retain the lead in a substantially fixed position relative to the cylindrical sleeve. If a burr hole ring is used and mounted in the cranium burr hole, the cylindrical sleeve and accompanying springs are inserted in the burr hole ring. The lead may then be inserted into the sleeve between the springs. The invention accepts the lead and fixes the lead in the desired position before the burr ring cap is placed over the burr hole ring. If a smaller diameter burr hole is desired, for example, 3 or 4 millimeters, the present invention may be used as a stand-alone anchoring device without a burr hole ring, which typically cannot accommodate the smaller size burr holes. With this embodiment, the cylindrical sleeve may have a threaded, serrated, or knurled outer wall which allows the sleeve to be retained in the burr hole. The lead may then be inserted into the sleeve between the springs.

Another embodiment of the present invention comprises generally a rotatable disk having a slot. Received within the rotatable disk is a sleeve defining a second slot for capturing and fixing the lead relative to the rotatable disk. The previously identified sleeve and spring assembly may also be mounted in the rotatable disk. Significantly, the rotatable disk permits the implanted lead to be positioned at any location within the burr hole ring and thus anywhere within the burr hole. This functional positioning of the lead within the burr hole compensates for any offset between the burr hole and the desired projection path of the lead. Consequently, with these preferred embodiments, the lead may be located and maintained in a fixed position relative to the brain to allow electrical stimulation and/or drug infusion to the targeted area with improved precision and accuracy.

Examples of the more important features of this invention have been broadly outlined above in order that the detailed description that follows may be better understood and so that contributions which this invention provides to the art may be better appreciated. There are, of course, additional features of the invention which will be described herein and which will be included within the subject matter of the claims appended hereto.

BRIEF DESCRIPTION OF THE DRAWINGS

The preferred embodiments of the invention will be described in relation to the accompanying drawings. In the drawings, the following figures have the following general nature:

FIG. 1 is a cross-section view of the lead fixation device of the present invention.

FIG. 2 is a top plan view of the invention of FIG. 1.

FIG. 3 is a cross-section view of the invention of FIG. 1.

FIG. 4 is an elevation view of a second embodiment of the lead fixation device of the present invention.

FIG. 5 is a plan view of the lead positioning device of the present invention.

FIG. 6 is another plan view of the invention of FIG. 5.

FIG. 7 is a cross-section view of the invention of FIG. 6.

In the accompanying drawings, like reference numbers are used throughout the various figures for identical structures.

DESCRIPTION OF THE PREFERRED EMBODIMENTS

Referring to FIGS. 1–3, a preferred medical lead and catheter fixation device is depicted. The preferred lead fixation device 10 may be used in conjunction with a standard cranial burr ring or as a stand-alone device implanted in a cranial burr hole. Whether or not a separate burr ring is used with a particular patient will depend on the specific circumstances involved in that patient's case. In addition, the lead fixation device 10 may also be used with the rotatable disc 50, described more fully below, which is mounted to a standard burr hole ring.

The lead fixation device 10 of the present invention defines a sleeve 12, preferably cylindrical in shape, and a lead-interactive member, preferably a plurality of springs 14. The lead fixation device 10 is designed to fit within a conventional burr hole ring, or the burr hole ring 52 more fully discussed below, which is then implanted in the cranium. A lead, or cannula if used, is then inserted into the lead fixation device 10. The lead is anchored within the fixation device with the end of the lead situated within the brain and positioned at the targeted stimulation area. As used herein, the term "lead" may refer to any elongated medical apparatus having an electrode providing electrical stimulation, or a parenchymal catheter for infusing pharmaceutical agents.

With regard to the burr rings, as one might imagine, there are many possible sizes and shapes. The selection of one burr ring over another will depend on numerous factors such as the size or shape of the burr hole. Thus, it should be understood that the following description, by way of example, shows exemplary burr ring configurations which may be used in connection with the present invention.

The lead fixation device 10 may be formed as a part of a separate member selectively attachable to the burr hole ring, or it may be formed as an integral portion of the burr hole ring. Again, the burr hole ring would typically be pre-placed within the pre-drilled burr hole, with the lead fixation device insertable into the pre-placed burr hole ring.

The sleeve 12, as depicted in FIGS. 1 and 2 as a cylindrical member, further defines inwardly extending circular shoulders 16, 18, a pair of opposing apertures 20, 22 at each end of the sleeve 12, and an inner wall 23. The sleeve 10 is preferably about 0.15–0.20 inches at its maximum outside diameter and has a preferable length of 0.20–0.30 inches. The sleeve may be made from a biocompatible material, such as, metal or plastic. Those skilled in the art will appreciate that the sleeve may incorporate a variety of other dimensions, depending on the chosen lead, burr hole ring and the desired application.

The inward circular shoulders 16, 18 are curved or angled at 21 to permit and control the bending of the lead. The curved shoulders allow the lead to be directed radially outward from the sleeve 12 and parallel to the cranium. A small flexible plug, not shown, may be inserted to engage the sleeve 12 and to close off either of the apertures 20, 22. Significantly, with the use of the lead-interactive members 14, the lead is stabilized prior to the placement of the flexible plug.

Seated between the shoulders 16, 18 of the sleeve 12 are the lead-interactive members 14, preferably springs. It is contemplated that other lead-interactive members may be used to fix the lead relative to the sleeve, and still be considered within the spirit and scope of the present invention. As most preferred, two pairs of opposing springs 14 are positioned within the sleeve 12. These four springs are positioned equidistant around the inner wall 23 of the sleeve 12 resulting in the two pairs of opposing spring sets. The number of springs and their configuration are dictated by the desired amount of radial force to be exerted on the lead. Thus, one should understand that other numbers, arrangements, shapes and sizes of springs may be used with the present invention, depending on the desired amount of radial force on the lead body. The springs 14 may be made of any biocompatible material that exhibits resiliency, such as, metal, plastic or rubber. The selection of the material is dictated, at least in part, by the desired spring force to be applied to the lead body.

The springs 14 are formed as thin, elongated members defining a curve 24 located near its longitudinal center. The curve 24 creates the resiliency of the spring 14. The overall length of the spring, in its unsprung state, is slightly less than the distance between the shoulders 16 and 18. As most preferred, the spring 14 is fixed at one end to the inner wall 23 and is free at its opposing end. That is, for example, the spring 14 is fixed to the inner wall 23 near the shoulder 16 and is free at the opposite spring end near the shoulder 18. Space is provided between the end of the spring 14 and the shoulder 18 to accommodate longitudinal movement of the spring end when the lead is inserted into the sleeve, compressing the spring 14. As preferred, the installed springs 14 create an opening through the sleeve 12 which has an unsprung diameter of 0.040–0.045 inches to accommodate a standard lead with an outer diameter of 0.050 inches. The unsprung diameter is selected to provide a certain radial force on the lead body. Accordingly, it will be appreciated by one skilled in the art that other unsprung diameters may be designed depending on the desired radial force to be exerted on the lead body.

Referring to FIG. 3, insertable within the sleeve 12 and between the springs 14 is the lead 31, or cannula if used. Once the lead 31 is inserted, the resilient springs 14 apply a radial force on the exterior surface of the lead body and, through friction forces between the springs and lead body, the lead is held in place in the desired location. If a cannula is used, the springs depress to accommodate the passage of the cannula through the sleeve 12. A lead is then inserted into the cannula. Once the cannula is removed leaving the lead in the desired position, the springs 14 snap back to engage the lead, thereby fixing it in place.

As conventional, the burr hole ring preferably has one or more lead guides to accept the lead once it has been inserted in the brain. These lead guides direct the lead radially outward from the center of the burr ring and substantially parallel to the cranium. A burr ring cap may then be placed over the burr hole ring and installed sleeve 12. Thus, the present invention fixes the lead in the desired position prior to the placement of the burr ring cap, thereby removing the possibility of lead movement during such cap placement.

Referring to FIG. 4, an alternative embodiment of the sleeve 12 is depicted. As preferred, the sleeve 30 is a stand-alone fixation device which is insertable directly into smaller cranial burr holes, for example, burr holes having a diameter of 3 to 4 millimeters. The sleeve 30 defines a cylindrical sleeve body 32 having either external serrations, threads or knurls 34, which stabilizes the sleeve 30 in the cranial burr hole. The sleeve 30 also has, at one end, a collar 36 defining an outwardly extending circular shoulder 38 and a tool engaging head 40. The remaining features of the sleeve 30 are the same as the sleeve 12, as depicted in FIG. 1. That is, the sleeve 30 also includes an inner cylindrical wall 23, apertures 20, 22, and inwardly extending shoulders 16, 18, which receive the lead-interactive members 14. Upon the insertion of the sleeve 30 into the burr hole in the cranium, the outwardly extending circular shoulder 38 serves to set the depth of the sleeve into the cranium and also serves as a stop to prevent the sleeve from passing through the cranium into the brain. The tool engaging head 40 is preferably hexagonal in shape for engaging a wrench which rotatably positions the sleeve 30 in the burr hole. It should be understood that other tool engaging heads may be used, such as, a round head having either a slot or an internal hexagon, for receiving other types of tools.

Referring to FIGS. 5–7, there is shown another embodiment of the present invention that allows the functional positioning of the lead within a cranium burr hole. This embodiment enhances the placement of the lead relative to the targeted stimulation area. As most preferred, a rotatable disc 50 is mounted within a burr hole ring 52. The rotatable disc 50 defines a slot 54 through the disc body which extends radially from the center of the disc to its periphery. Positioned within the slot 54 is the sleeve 30 or, preferrably, the lead fixation member 56. The lead fixation member 56 defines a cylindrical sleeve 58 having an integral circular shoulder 60, and a slot 62 for capturing and fixing the lead body. In use, the sleeve 58 is inserted through the slot 54 with the shoulder 60 seated against the rotatable disc 50. The sleeve 58 has an external diameter that permits the slidable engagement with the slot 54. Significantly, the lead fixation member 56 may be located at any position along the slot 54. Further, with the disc 50 being rotatable within the burr hole ring 52, the fixation member 56 may be located at any position within the burr hole ring. That is, the lead fixation member 56 may slide within the slot 54 and be rotated within the burr hole ring 52, permitting full degree of motion of the fixation member 56 within the burr hole.

The preferred embodiments of the invention are now described as to enable a person of ordinary skill in the art to make and use the same. Variations of the preferred embodiment are possible without being outside the scope of the present invention. Therefore, to particularly point out and distinctly claim the subject matter regarded as the invention, the following claims conclude the specification.

What is claimed is:

1. A medical apparatus for fixing a lead or catheter in a cranium burr hole comprising:
   a sleeve having inwardly extending shoulders, and
   a plurality of springs positioned within the sleeve and between the shoulders, whereby the lead is selectively positioned within the sleeve and fixedly held by the plurality of springs relative to the sleeve.

2. The medical apparatus of claim 1 wherein the plurality of springs are two pairs of opposing springs positioned within the sleeve.

3. The medical apparatus of claim 1 wherein the sleeve is cylindrical.

4. The medical apparatus of claim 3 wherein the cylindrical sleeve has two ends, each end defining the inwardly extending shoulders and forming an aperture.

5. The medical apparatus of claim 4 wherein the cylindrical sleeve defines an inner cylindrical wall.

6. The medical apparatus of claim 5 wherein the springs are located between the inwardly extending shoulders adjacent the inner cylindrical wall.

7. The medical apparatus of claim 1 wherein the sleeve further defines an outwardly extending shoulder.

8. The medical apparatus of claim 1 wherein the sleeve further defines an outer surface that is serrated.

9. The medical apparatus of claim 1 wherein the sleeve further defines an outer surface that is threaded.

10. The medical apparatus of claim 1 wherein the sleeve further defines an outer surface that is knurled.

11. A medical apparatus for fixing a lead or catheter in a cranium burr hole comprising:
    a sleeve for receiving the lead, and
    a lead-interactive member positioned within the sleeve, the lead-interactive member configured to radially position the lead, to reduce loading of the lead, and to maintain the desired lead projection path,
    whereby the lead is selectively positioned within the sleeve and fixedly held by the lead-interactive member relative to the sleeve.

12. The medical apparatus of claim 11 wherein the sleeve defines inwardly extending shoulders, the lead-interactive member positioned between the inwardly extending shoulders.

13. The medical apparatus of claim 11 wherein the sleeve defines an outwardly extending shoulder.

14. The medical apparatus of claim 11 wherein the sleeve further defines an outer surface that is serrated.

15. The medical apparatus of claim 11 wherein the sleeve further defines an outer surface that is threaded.

16. The medical apparatus of claim 11 wherein the sleeve further defines an outer surface that is knurled.

17. The medical apparatus of claim 11 wherein the lead-interactive member defines at least one resilient body positioned within the sleeve.

18. The medical apparatus of claim 17 wherein the resilient body is a spring.

19. The medical apparatus of claim 11 wherein the reduced loading of the lead reduces lead tip migration from a lead tip target.

20. The medical apparatus of claim 11 wherein the lead is fixedly held by the lead-interactive member before a burr cap ring is installed to reduce inadvertant lead movement during burr cap ring installation.

21. A medical lead fixation device for anchoring a lead or catheter to the cranium comprising:
    a burr hole ring,
    a sleeve mounted within the burr hole ring, and
    a lead-interactive member mounted within the sleeve, the lead-interactive member configured to radially position the lead, to reduce loading of the lead, and to maintain the desired lead projection path,
    whereby the lead is selectively positioned within the sleeve and fixedly held by the lead-interactive member relative to the burr hole ring.

22. The medical lead fixation device of claim 21 further comprising a burr ring cap positioned over the burr hole ring.

23. The medical lead fixation device of claim 21 wherein the lead-interactive member is at least one resilient member.

24. The medical lead fixation device of claim 23 wherein the at least one resilient member is a spring.

25. The medical lead fixation device of claim 23 wherein the sleeve defines opposing inwardly extending shoulders, the at least one resilient member positioned within the sleeve and between the inwardly extending shoulders.

26. The medical lead fixation device of claim 21 wherein the sleeve is cylindrical.

27. The medical apparatus of claim 21 wherein the sleeve further defines an outer surface that is serrated.

28. The medical apparatus of claim 21 wherein the sleeve further defines an outer surface that is threaded.

29. The medical apparatus of claim 21 wherein the sleeve further defines an outer surface that is knurled.

30. The medical lead fixation device of claim 21 wherein the reduced loading of the lead reduces lead tip migration from a lead tip target.

31. The medical lead fixation device of claim 21 wherein the lead is fixedly held by the lead-interactive member before a burr cap ring is installed to reduce inadvertant lead movement during burr cap ring installation.

32. A method for fixing a medical lead or catheter in a cranial burr hole, comprising the steps of:
   implanting a cranial burr hole ring in the cranial burr hole,
   providing a cylindrical sleeve,
   providing a lead-interactive member, the lead-interactive member mounted within the cylindrical sleeve and configured to radially position the lead, to reduce loading of the lead and to maintain the desired lead projection path,
   mounting the cylindrical sleeve within the cranial burr hole ring, and
   inserting the lead into the cylindrical sleeve.

33. The method for fixing a medical lead or catheter of claim 32 wherein the lead-interactive member is a plurality of resilient members.

34. The method for fixing a medical lead or catheter of claim 33 further comprising the step of positioning the lead between the plurality of resilient members.

35. A medical apparatus for positioning and fixing a lead or catheter in a cranial burr hole comprising:
   a burr hole ring,
   a disc mounted to the burr hole ring, the disc defining a slot, and
   a sleeve mounted within the slot of the disc.

36. The medical apparatus of claim 35 wherein the sleeve is cylindrical and defines an outwardly extending shoulder and a lead-interactive member.

37. The medical apparatus of claim 36 wherein the lead-interactive member is a second slot.

38. The medical apparatus of claim 36 wherein the lead-interactive member is a plurality of resilient members positioned around the lead.

39. The medical apparatus of claim 38 wherein the plurality of resilient members are springs.

40. The medical apparatus of claim 35 wherein the disc defines a center and a periphery, the slot extending from the center to the periphery of the disc.

41. A medical apparatus for positioning and fixing a lead or catheter in a cranial burr hole comprising:
   a burr hole ring,
   a disc mounted to the burr hole ring, the disc defining a slot,
   a sleeve mounted within the slot of the disc, and
   a lead-interactive member mounted within the sleeve.

42. The medical apparatus of claim 41 wherein the lead-interactive member is a plurality of resilient members.

43. The medical apparatus of claim 42 wherein the plurality of resilient members are springs.

44. The medical apparatus of claim 41 wherein the lead-interactive member is a second slot.

45. The medical apparatus of claim 41 wherein the sleeve is cylindrical.

46. The medical apparatus of claim 41 wherein the sleeve defines an outwardly extending shoulder.

47. A medical lead positioning device for selectively locating a lead or catheter within a cranial burr hole comprising:
   a burr ring,
   a disc mountable within the burr ring, the disc defining a first slot, and
   a cylindrical sleeve having an outwardly extending shoulder, the sleeve mountable within the first slot of the disc, the sleeve further defining a second slot.

48. A method for positioning and fixing a medical lead or catheter in a cranial burr hole, comprising the steps of:
   implanting a cranial burr hole ring in the cranial burr hole,
   mounting a disc within the cranial burr hole ring, the disc defining a slot,
   mounting a cylindrical sleeve within the slot of the disc,
   providing a lead-interactive member, the lead-interactive member mounted within the cylindrical sleeve,
   inserting the lead into the cylindrical sleeve,
   locating the lead within the cranial burr hole ring, and
   holding the lead within the lead-interactive member and relative to the cranial burr hole ring.

* * * * *